(12) United States Patent
Stenzel et al.

(10) Patent No.: US 6,303,598 B1
(45) Date of Patent: Oct. 16, 2001

(54) FUNGICIDAL ACTIVE SUBSTANCE COMBINATIONS

(75) Inventors: Klaus Stenzel, Düsseldorf; Stefan Dutzmann, Langenfeld; Ulrich Heinemann, Leichlingen, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/729,879

(22) Filed: Dec. 5, 2000

Related U.S. Application Data

(62) Division of application No. 09/319,400, filed as application No. PCT/EP97/06616 on Nov. 27, 1997, now Pat. No. 6,191,128.

(30) Foreign Application Priority Data

Dec. 10, 1996 (DE) ................................. 196 51 217
Feb. 11, 1997 (DE) ................................. 197 05 159
Sep. 11, 1997 (DE) ................................. 197 39 982

(51) Int. Cl.⁷ ......................... A61K 31/535; A01N 43/54
(52) U.S. Cl. ...................................... 514/229.2; 514/275
(58) Field of Search ................................. 514/229.2, 275

(56) References Cited

U.S. PATENT DOCUMENTS 4,931,566 * 6/1990 Hubele .................................. 544/315

FOREIGN PATENT DOCUMENTS 196 20 095 7/1997 (EP) .
97/27189 7/1997 (WO) .

OTHER PUBLICATIONS

Tomlin, The Pesticide Manual Incorporating The Agrochemicals Handbook, 10ᵗʰ Ed. (1995) pp. 652, 885 and 886.*

K.H. Büchel Pflanzenschutz und Schädlingsbekämpfung pp. 87, 136, 140, 141 & 153, (month unavailable) 1977, George Thieme Verlag, Stuttgart.

S.R. Colby, Weeds, 15, (month unavailable) 1967, pp. 20–22.

* cited by examiner

*Primary Examiner*—Allen J. Robinson
(74) *Attorney, Agent, or Firm*—Joseph C. Gil

(57) ABSTRACT

Novel active compound combinations comprising a compound of the formula (I)

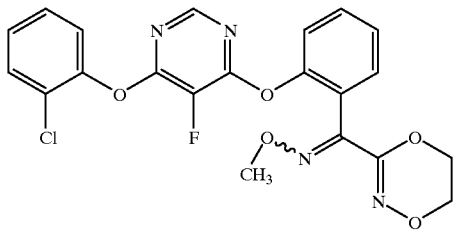

(I)

and known fungicidally active compounds, and their use for controlling phytopathogenic fungi, are described.

5 Claims, No Drawings

FUNGICIDAL ACTIVE SUBSTANCE COMBINATIONS

This application is a divisional application of U.S. application Ser. No. 09/319,400, filed on Jun. 2, 1999 now U.S. Pat. No. 6,191,128, which is a 371 of PCT/EP97/06616, filed Nov. 27, 1997.

TECHNICAL FIELD OF THE INVENTION

The present application relates to novel active compound combinations which are highly suitable for controlling phytopathogenic fungi and which comprise a compound of the formula (I)

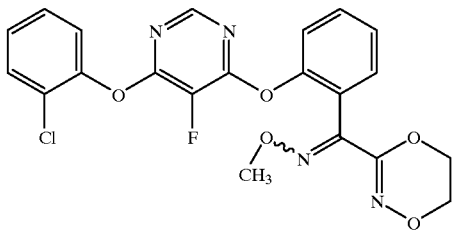

and other known fungicidally, active compounds.

BACKGROUND OF THE INVENTION

It is already known that the compound of the formula (I) has fungicidal properties (DE-19 602 095). The activity of this compound is good; however, it is not always satisfactory at low application rates.

Furthermore, it is already, known that a large number of azole derivatives, aromatic carboxylic acid derivatives, morpholine compounds and other heterocycles can be employed for controlling fungi (cf. K. H. Buchel "Pflanzenschutz und Schädlingsbekämpfung", pages 87, 136, 140, 141 and 146 to 153, Georg Thieme Verlag. Stuttgart 1977). However, the activity of the compounds in question is not always satisfactor at low application rates.

DETAILED DESCRIPTION OF THE INVENTION

The present invention, accordingly, provides the novel active compound combinations comprising a compound of the formula (I)

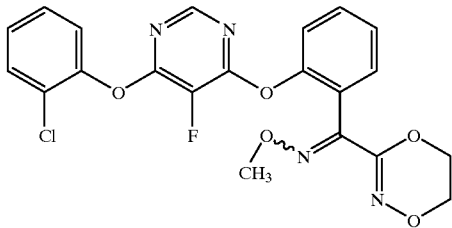

and at least one mixing partner
(A) Antracol (propineb) and/or
(B) Euparene (dichlorofluanide) and/or Euparene M (tolylfluatide) and/or
(C) bitertanol and/or
(D) tebuconazole and/or
(E) triadimefon and/or
(F) triadimenol and/or
(G) imidacloprid and/or
(H) Sumisclex and/or
(II) mancozeb and/or
(K) folpet (Phaltan) and/or
(L) dimetomorph and/or
(M) cymoxanil and/or
(N) metalaxyl and/or
(O) Aliette (fosetyl-Al) and/or
(P) famoxadone and/or
(Q) pyrimethanil and/or
(R) cyprodinyl and/or
(S) mepanipyrim and/or
(T) kresoxim-methyl and/or
(U) azoxystrobin and/or
(V) epoxiconazole and/or
(W) metconazole and/or
(X) fluquinconazole and/or
(Y) fludioxonil and/or
(Z) fenpiclonil and/or
($\alpha$) guazatine and/or
($\beta$) Bione and/or
($\chi$) 1-methylethyl [2-methyl-1-[[[1-(4-methylphenyl)ethyl]amino]carbonyl]-propyl]carboxylic acid and/or
($\delta$) 8-t-butyl-2-(N-ethyl-N-n-propyl-amino)-methyl-1,4-dioxaspiro[5.4]-decane and/or
($\epsilon$) 2,3-dichloro-4-(1-methylcyclohexylcarbonylamino)-phenol and/or
($\omega$) N-(R)-[1-(4-chloro-phenyl)-ethyl]-2,2-dichloro-1-ethyl-3t-methyl-1r-cyclopropane-carboxamide and/or
($\pi$) fluazinam and/or
($\theta$) captan and/or
($\rho$) Monceren (pencycuron) and/or
($\sigma$) fenpiclonil
which have very good fungicidal properties which complement each other synergistically.

The active compound of the formula (I) is known (DE-19 602 095). The other components which are present in the combinations according to the invention are also known.

In addition to the active compound of the formula (I), the active compound combinations according to the invention comprise at least one active compound from the compounds (A) to ($\sigma$). However, further fungicidally active additives may additionally be present.

The synergistic effect is particularly pronounced when the active compounds in the active compound combinations according to the invention are present in certain weight ratios. However, the weight ratios of the active compounds in the active compound combinations can be varied within relatively broad ranges. In general, there are 0.01 to 50, preferably 0.25 to 20, parts by weight of the active compounds (A) to ($\sigma$) per part by weight of active compound of the formula (I).

In particular, there are the stated parts by weight of the following mixing partners per part by weight of the compound of the formula (I):

| | | | |
|---|---|---|---|
| (A) | 1:1 to 1:50 | preferably | 1:5 to 1:20, |
| (B) | 1:1 to 1:50 | preferably | 1:5 to 1:20, |
| (C) | 10:1 to 1:10 | preferably | 5:1 to 1:5, |
| (D) | 10:1 to 1:10 | preferably | 5:1 to 1:5, |
| (E) | 10:1 to 1:10 | preferably | 5:1 to 1:5, |
| (F) | 10:1 to 1:10 | preferably | 5:1 to 1:5, |
| (G) | 20:1 to 1:20 | preferably | 10:1 to 1:10, |
| (H) | 10:1 to 1:10 | preferably | 5:1 to 1:5, |
| (II) | 1:1 to 1:50 | preferably | 1:5 to 1:20, |

| | -continued | | |
|---|---|---|---|
| (K) | 1:1 to 1:50 | preferably | 1:5 to 1:20, |
| (L) | 10:1 to 1:10 | preferably | 5:1 to 1:5, |
| (M) | 10:1 to 1:10 | preferably | 5:1 to 1:5, |
| (N) | 10:1 to 1:10 | preferably | 5:1 to 1:5, |
| (O) | 10:1 to 1:50 | preferably | 1:1 to 1:10, |
| (P) | 10:1 to 1:10 | preferably | 5:1 to 1:5, |
| (Q) | 5:1 to 1:20 | preferably | 1:1 to 1:10, |
| (R) | 5:1 to 1:20 | preferably | 1:1 to 1:10, |
| (S) | 5:1 to 1:20 | preferably | 1:1 to 1:10, |
| (T) | 10:1 to 1:10 | preferably | 5:1 to 1:5, |
| (U) | 10:1 to 1:10 | preferably | 5:1 to 1:5, |
| (V) | 10:1 to 1:10 | preferably | 5:1 to 1:5, |
| (W) | 10:1 to 1:10 | preferably | 5:1 to 1:5, |
| (X) | 10:1 to 1:10 | preferably | 5:1 to 1:5, |
| (Y) | 10:1 to 1:10 | preferably | 5:1 to 1:5, |
| (Z) | 10:1 to 1:10 | preferably | 5:1 to 1:5, |
| ($\alpha$) | 10:1 to 1:10 | preferably | 5:1 to 1:5, |
| ($\beta$) | 50:1 to 1:50 | preferably | 20:1 to 1:10, |
| ($\chi$) | 10:1 to 1:10 | preferably | 5:1 to 1:5, |
| ($\delta$) | 10:1 to 1:20 | preferably | 5:1 to 1:10, |
| ($\epsilon$) | 10:1 to 1:10 | preferably | 5:1 to 1:5, |
| ($\omega$) | 10:1 to 1:10 | preferably | 5:1 to 1:5, |
| ($\pi$) | 10:1 to 1:10 | preferably | 5:1 to 1:5, |
| ($\theta$) | 5:1 to 1:50 | preferably | 1:1 to 1:20, |
| ($\rho$) | 10:1 to 1:10 | preferably | 4:1 to 1:4, |
| ($\sigma$) | 10:1 to 1:10 | preferably | 4:1 to 1:4 |

The active compound combinations according to the invention have very good fungicidal properties and can be employed in particular for controlling phytopathogenic fungi, such as Plasmodiophoromycetes, Oomycetes, Chytridiomycetes, Zygomycetes, Ascomycetes, Basidiomycetes and Deuteromycetes, etc.

The active compound combinations according to the invention are particularly suitable for controlling cereal diseases, such as Erysiphe, Cochliobolus, Pyrenophora, RPhynchosporium, Septoria spp., Fusarium spp., Pseudocercosporella and Leptosphaeria, and for controlling fungal infections of non-cereal crops such as wine, fruit, vegetables, for example Phytophthora, Plasmopara, Pythium, and powdery mildew fungi such as, for example, Sphaerotheca or Uncinula, and causative organisms of leaf spot such as Venturia, Altemaria and Septoria, and Rhizoctonia, Botrytis, Sclerotinia and Sclerotium.

The fact that the active compound combinations are well tolerated by plants at the concentrations required for controlling plant diseases permits the treatment of aerial parts of plants, of propagation stock and seeds, and of the soil.

The active compound combinations according to the invention can be converted to the customary formulations, such as solutions, emulsions, suspensions, powders, foams, pastes, granules, aerosols and microencapsulations in polymeric substances and in coating compositions for seeds, and ULV formulations.

These formulations are produced in a known manner, for example by mixing the active compounds or active compound combinations with extenders, that is liquid solvents, liquefied gases under pressure, and/or solid carriers, optionally with the use of surfactants, that is emulsifiers and/or dispersants, and/or foam formers. If the extender used is water, it is also possible to use, for example, organic solvents as auxiliary solvents. Essentially, suitable liquid solvents include: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, or else water. Liquefied gaseous extenders or carriers are to be understood as meaning liquids which are gaseous at ambient temperature and under atmospheric pressure, for example aerosol propellants such as halogenated hydrocarbons and butane, propane, nitrogen and carbon dioxide. Suitable solid carriers are: for example ground natural minerals such as kaolins, clays, talc, chalk, quartz, attapulgite, montmorillonite or diatomaceous earth, and ground synthetic minerals such as finely divided silica, alumina and silicates. Suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks. Suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates. Suitable dispersants are: for example lignin-sulphite waste liquors and methylcellulose.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other additives can be mineral and vegetable oils.

It is possible to use colourants such as inorganic pigments, for example iron oxide, titanium oxide and prussian blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95% by weight of active compound, preferably between 0.5 and 90%.

In the formulations, the active compound combinations according to the invention can be present as a mixture with other known active compounds such as fungicides, insecticides, acaricides and herbicides, and as mixtures with fertilizers or plant growth regulators.

The active compound combinations can be used as such, in the form of their formulations or as the use forms prepared therefrom, such as ready-to-use solutions, emulsifiable concentrates, emulsions, suspensions, wettable powders, soluble powders and granules.

They are used in the customary manner, for example by watering, spraying, atomizing, scattering, spreading, and as a powder for dry seed treatment, a solution for seed treatment, a water-soluble powder for seed treatment, a water-soluble powder for slurry treatment, or by encrusting.

In the treatment of parts of plants, the active compound concentrations in the use forms can be varied within a relatively wide range. In general, they are between 1 and 0.0001% by weight, preferably between 0.5 and 0.001%.

In the treatment of seeds, amounts of 0.001 to 50 g of active compound per kilogram of seeds are generally required, preferably 0.01 to 10 g.

In the treatment of the soil, active compound concentrations of 0.00001 to 0.1% by weight, preferably of 0.0001 to 0.02% by weight, are required at the site of action.

The good fungicidal, synergistic activity of the active compound combinations according to the invention is evident from the examples below. While the individual active compounds exhibit weaknesses with regard to the fungicidal activity, the combinations have an activity which exceeds a simple addition of activities.

A synergistic effect of fungicides is always present when the fungicidal activity of the active compound combinations exceeds the total of he activities of the active compounds when applied individually.

The expected activity for a given combination of two active compounds can be calculated as follows (cf. Colby, S. R., "Calculating Synergistic and Antagonistic Responses of Fierbicide Combinations", Weeds 15, pages 20–22, 1967):

If

X is the efficacy expressed in % of the untreated control when applying active compound A in a concentration of m ppm, Y is the efficacy expressed in % of the untreated control when applying active compound B at a concentration of n ppm, E is the expected efficacy expressed in % of the untreated control when applying the active substances A and B at a concentration of m and n ppm, respectively, then $$E = X + Y - \frac{X \cdot Y}{100}$$

If the actual fungicidal activity exceeds the calculated value, then the activity of the combination is superadditive, i.e. a synergistic effect exists. In this case, the efficacy which was actually observed must be greater than the value for the expected efficacy (E) calculated from the abovementioned formula:

EXAMPLE 1

Phytophthora Test (Tomato)/Protective

To test for protective activity, young plants are sprayed with the commercial active compound preparation at the stated application rate. After the spray coating has dried on, the plants are inoculated with an aqueous spore suspension of *Phytophthora infestans*. The plants then remain in an incubation cabin at about 20° C. and 100% relative atmospheric humidity.

Evaluation is carried out 3 days after the inoculation. 0% means an efficacy corresponding to that of the control, and an efficacy of 100% means that no infection is observed.

The good fungicidal activity of the active compound combinations according to the invention is evident from the example below. While the individual active compounds exhibit weaknesses with regard to the fungicidal activity, the combinations have an activity which exceeds a simple addition of activities.

A synergistic effect of fungicides is always present when the fungicidal activity of the active compound combinations exceeds the total of the activities of the active compounds when applied individually.

The expected activity for a given combination of two active compounds can be calculated as follows (cf. Colby, S. R., "Calculating Synergistic and Antagonistic Responses of Herbicide Combinations", Weeds 15, pages 20–22, 1967):

If

X is the efficacy expressed in % of the untreated control when applying active compound A in a concentration of rn ppm, Y is the efficacy expressed in % of the untreated control when applying active compound B at a concentration of n ppm, E is the expected efficacy expressed in % of the untreated control when applying the active substances A and B at a concentration of m and n ppm, respectively, then $$E = X + Y - \frac{X \times Y}{100}$$

If the actual fungicidal activity exceeds the calculated value, then the activity of the combination is superadditive, i.e. a synergistic effect exists. In this case, the efficacy which was actually observed must be greater than the value for the expected efficacy (E) calculated from the abovementioned formula.

The table below clearly shows that the observed activity of the active compound combination according to the invention is greater than the calculated activity, i.e. a synergistic effect is present.

TABLE 1

| Phytophtora test (tomato)/protective | | |
|---|---|---|
| Active compound | Active compound application rate in g/ha | % efficacy |
| (I) 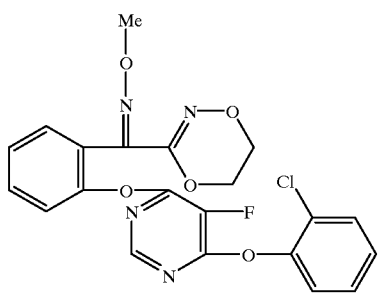 | 0.5 | 9 |
| (χ) | 0.5 | 20 |

TABLE 1-continued

Phytophtora test (tomato)/protective

[Chemical structure: H₃C—CH(CH₃)—O—C(=O)—NH—CH(CH(CH₃)CH₃)—C(=O)—NH—CH(CH₃)—C₆H₄—CH₃]

Racemic amide of L-valine

| | Mixture according to the invention: | | | |
|---|---|---|---|---|
| | Mixing ratio | Active compound application rate in g/ha | Actual efficacy | Expected value, calculated using Colby's formula |
| (I) (χ) | 1:1 | 0.5 + 0.5 | 77 | 27 |

| Active compound | Active compound application rate in g/ha | % efficacy |
|---|---|---|
| (I) | 5 | 45 |

[Chemical structure of compound (I)]

| Tebuconazole (D) | 5 | 26 |

[Chemical structure of Tebuconazole: Cl—C₆H₄—CH₂—CH₂—C(tBu)(OH)—CH₂—N(triazole)]

| | Mixture according to the invention: | | | |
|---|---|---|---|---|
| | Mixing ratio | Active compound application rate in g/ha | Actual efficacy | Expected value, calculated using Colby's formula |
| (I) (D) | 1:1 | 5 + 5 | 84 | 59 |

| Active compound | Active compound application rate in g/ha | % efficacy |
|---|---|---|
| (I) | 5 | 45 |

[Chemical structure of compound (I)]

| Triadimenol (F) | 5 | 0 |

TABLE 1-continued

Phytophtora test (tomato)/protective

[Chemical structure: triadimenol - (CH3)3C-CH(OH)-CH(-O-C6H4-Cl)-N(triazole)]

Mixture according to the invention:

| | Mixing ratio | Active compound application rate in g/ha | Actual efficacy | Expected value, calculated using Colby's formula |
|---|---|---|---|---|
| (I) (F) | 1:1 | 5 + 5 | 72 | 45 |

| Active compound | Active compound application rate in g/ha | % efficacy |
|---|---|---|
| (I) | 5 | 45 |

[Chemical structure with methoxyimino group, pyrimidine, fluoro, chlorophenoxy]

| | | |
|---|---|---|
| (ε) | 5 | 14 |

[Chemical structure: 2,3-dichloro-4-hydroxyphenyl cyclohexane carboxamide]

Mixture according to the invention:

| | Mixing ratio | Active compound application rate in g/ha | Actual efficacy | Expected value, calculated using Colby's formula |
|---|---|---|---|---|
| (I) (ε) | 1:1 | 5 + 5 | 82 | 53 |

| Active compound | Active compound application rate in g/ha | % efficacy |
|---|---|---|
| (I) | 5 | 45 |

TABLE 1-continued

Phytophtora test (tomato)/protective

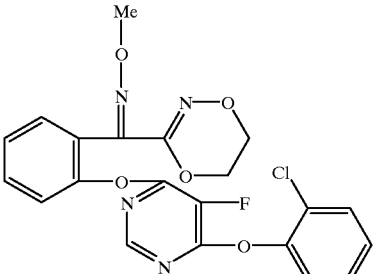

(ω)

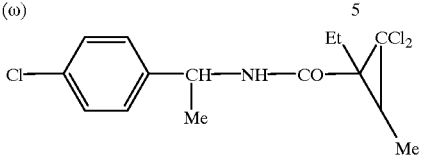

Mixture according to the invention:

| | Mixing ratio | Active compound application rate in g/ha | Actual efficacy | Expected value, calculated using Colby's formula |
|---|---|---|---|---|
| (I) + (ω) | 1:1 | 5 + 5 | 71 | 47 |

| Active compound | Active compound application rate in g/ha | % efficacy |
|---|---|---|
| (I) | 5 | 45 |

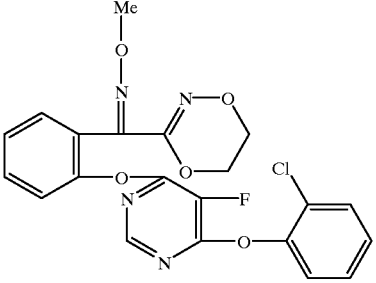

(H)

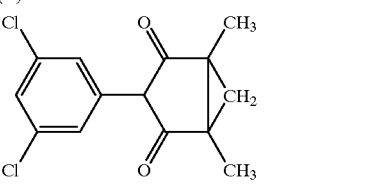

Mixture according to the invention:

| | Mixing ratio | Active compound application rate in g/ha | Actual efficacy | Expected value, calculated using Colby's formula |
|---|---|---|---|---|
| (I) + Procymidone | 1:1 | 5 + 5 | 75 | 64 |

| Active compound | Active compound application rate in g/ha | % efficacy |
|---|---|---|
| (I) | 5 | 45 |

TABLE 1-continued

Phytophtora test (tomato)/protective

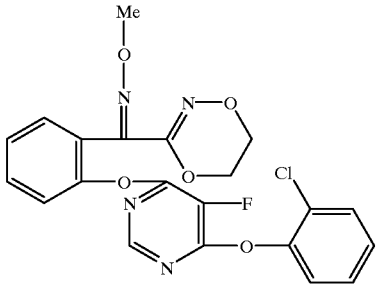

| | | | |
|---|---|---|---|
| Mancozeb (II) H₂C—NH—CS—S\\Mn / H₂C—NH—CS—S | | 50 | 54 |

Mixture according to the invention:

| | Mixing ratio | Active compound application rate in g/ha | Actual efficacy | Expected value, calculated using Colby's formula |
|---|---|---|---|---|
| (I) + Mancozeb (II) | 1:10 | 5 + 5 | 89 | 75 |

| Active compound | Active compound application rate in g/ha | % efficacy |
|---|---|---|
| (I) | 1 | 20 |

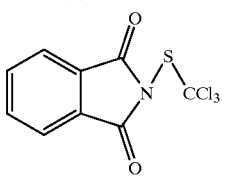

| | | | |
|---|---|---|---|
| Phaltan (K) | | 10 | 27 |

Mixture according to the invention:

| | Mixing ratio | Active compound application rate in g/ha | Actual efficacy | Expected value, calculated using Colby's formula |
|---|---|---|---|---|
| (I) + Phaltan | 1:10 | 1 + 10 | 74 | 42 |

| Active compound | Active compound application rate in g/ha | % efficacy |
|---|---|---|
| (I) | 1 | 20 |

TABLE 1-continued

Phytophtora test (tomato)/protective

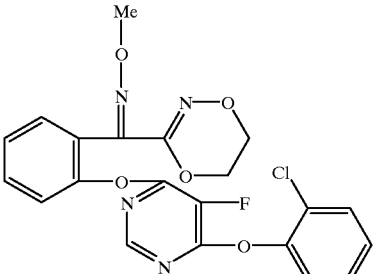

| | Dimetomorph (L) | 1 | 0 |

Mixture according to the invention:

| | Mixing ratio | Active compound application rate in g/ha | Actual efficacy | Expected value, calculated using Colby's formula |
|---|---|---|---|---|
| (I) + Dimetomorph (L) | 1:1 | 1 + 1 | 49 | 20 |

| Active compound | Active compound application rate in g/ha | % efficacy |
|---|---|---|
| (I) | 5 | 45 |
| Cymoxanil (M) | 5 | 12 |

Mixture according to the invention:

| | Mixing ratio | Active compound application rate in g/ha | Actual efficacy | Expected value, calculated using Colby's formula |
|---|---|---|---|---|
| (I) + Cymoxanil | 1:1 | 5 + 5 | 78 | 52 |

| Active compound | Active compound application rate in g/ha | % efficacy |
|---|---|---|

TABLE 1-continued

Phytophtora test (tomato)/protective

| | Active compound application rate in g/ha | % efficacy |
|---|---|---|
| (I) [structure shown] | 5 | 45 |
| Metalaxyl (N) [structure shown] | 5 | 1 |

Mixture according to the invention:

| | Mixing ratio | Active compound application rate in g/ha | Actual efficacy | Expected value, calculated using Colby's formula |
|---|---|---|---|---|
| (I) + (N) | 1:1 | 5 + 5 | 62 | 46 |

| Active compound | Active compound application rate in g/ha | % efficacy |
|---|---|---|
| (I) [structure shown] | 5 | 45 |
| Fluazinam (π) [structure shown] | 5 | 11 |

Mixture according to the invention:

| | Mixing ratio | Active compound application rate in g/ha | Actual efficacy | Expected value, calculated using Colby's formula |
|---|---|---|---|---|
| (I) + Fluazinam (π) | 1:1 | 5 + 5 | 85 | 51 |

| Active compound | Active compound application rate in g/ha | % efficacy |
|---|---|---|

TABLE 1-continued

Phytophtora test (tomato)/protective

| Compound | Application rate (g/ha) | % efficacy |
|---|---|---|
| (I) [structure: Me-O-N=C linked to N-O containing ring, with O linked to pyrimidine bearing F and O-(2-chlorophenyl)] | 5 | 45 |
| Cyprodinyl (R) [structure: 4-cyclopropyl-6-methyl-2-(phenylamino)pyrimidine] | 5 | 0 |

Mixture according to the invention:

| | Mixing ratio | Active compound application rate in g/ha | Actual efficacy | Expected value, calculated using Colby's formula |
|---|---|---|---|---|
| (I) + Cyprodinyl | 1:1 | 5 + 5 | 62 | 45 |

| Active compound | Active compound application rate in g/ha | % efficacy |
|---|---|---|
| (I) [structure: same as above] | 1 | 20 |
| Kresoxime-methyl (T) [structure: methyl (E)-2-methoxyimino-2-[2-(o-tolyloxymethyl)phenyl]acetate] | 1 | 14 |

Mixture according to the invention:

| | Mixing ratio | Active compound application rate in g/ha | Actual efficacy | Expected value, calculated using Colby's formula |
|---|---|---|---|---|
| (I) | | 1 | | |

TABLE 1-continued

| Phytophtora test (tomato)/protective | | | | |
|---|---|---|---|---|
| + Kresoxime-methyl (T) | 1:1 | + 1 | 64 | 31 |

| Active compound | Active compound application rate in g/ha | % efficacy |
|---|---|---|
| (I) 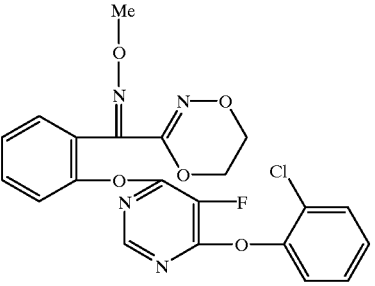 | 5 | 45 |
| Bendicar (Bion) (β) | 5 | 0 |

| Mixture according to the invention: | | | |
|---|---|---|---|
| | Mixing ratio | Active compound application rate in g/ha | Actual efficacy | Expected value, calculated using Colby's formula |
| (I) + Bendicar | 1:1 | 5 + 5 | 54 | 45 |

EXAMPLE 2
Sphaerotheca Test (Cucumber)/Protective

To test for protective activity, young plants are sprayed with the commercial active compound preparation at the stated application rate. After the spray coating has dried on, the plants are inoculated with an aqueous spore suspension of *Sphaerotheca fuliginea*. The plants then remain in a greenhouse at about 23° C. and about 70% relative atmospheric humidity.

Evaluation is carried out 10 days after the inoculation. 0% means an efficacy corresponding to that of the control, and an efficacy of 100% means that no infection is observed.

The good fungicidal activity of the active compound combinations according to the invention is evident from the example below. While the individual active compounds exhibit weaknesses with regard to the fungicidal activity, the combinations have an activity which exceeds a simple addition of activities.

A synergistic effect of fungicides is always present when the fungicidal activity of the active compound combinations exceeds the total of the activities of the active compounds when applied individually.

The expected activity for a given combination of two active compounds can be calculated as follows (cf. Colby, S. R., "Calculating Synergistic and Antagonistic Responses of Herbicide Combinations", Weeds 15, pages 20–22, 1967):

If

X is the efficacy expressed in % of the untreated control when applying active compound A in a concentration of m ppm, Y is the efficacy expressed in % of the untreated control when applying active compound B at a concentration of n ppm, E is the expected efficacy expressed in % of the untreated control when applying the active substances A and B at a concentration of m and n ppm, respectively, then $$E = X + Y - \frac{X \times Y}{100}$$

If the actual fungicidal activity exceeds the calculated value, then the activity of the combination is superadditive, i.e. a synergistic effect exists. In this case, the efficacy which was actually observed must be greater than the value for the expected efficacy (E) calculated from the abovementioned formula.

The table below clearly shows that the observed activity of the active compound combination according to the invention is greater than the calculated activity, i.e. a synergistic effect is present.

TABLE 2

| Sphaerotheca test (cucumber)/protective | | |
|---|---|---|
| Active compound | Active compound application rate in g/ha | % efficacy |

TABLE 2-continued

| Active compound | | | | | Active compound application rate in g/ha | % efficacy |
|---|---|---|---|---|---|---|

(I) — [structure: methoxyimino compound with dioxazine ring, linked via pyrimidine with F and O-(2-chlorophenyl)] — 2.5 — 22

Propineb (A) — —[Zn—S—CS—NH—CH₂—CH(CH₃)—NH—CS—S]ₙ— — 25 — 45 n = >1

Mixture according to the invention:

| Mixing ratio | Active compound application rate in g/ha | Actual efficacy | Expected value, calculated using Colby's formula |
|---|---|---|---|
| (I) + Propineb     1:10 | 2.5 + 25 | 77 | 56 |

Sphaerotheca test (cucumber)/protective

| Active compound | Active compound application rate in g/ha | % efficacy |
|---|---|---|

(I) — [same structure as above] — 2.5 — 22

Dichlorofluanid (B1) — $(CH_3)_2$—N—$SO_2$—N(C₆H₅)—S—$CCl_2F$ — 25 — 20

Mixture according to the invention:

| Mixing ratio | Active compound application rate in g/ha | Actual efficacy | Expected value, calculated using Colby's formula |
|---|---|---|---|
| (I) + Dichlorofluanid     1:10 | 2.5 + 25 | 57 | 38 |

Sphaerotheca test (cucumber)/protective

| Active compound | Active compound application rate in g/ha | % efficacy |
|---|---|---|

TABLE 2-continued

| | | | | 2.5 | 22 |
|---|---|---|---|---|---|
| (I) | 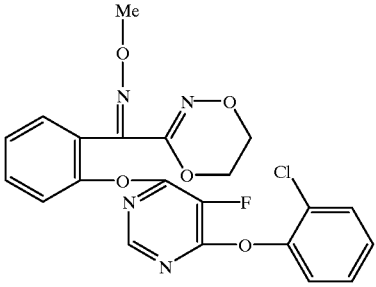 | | | | |
| Tolyfluanid (B2) | (CH₃)₂—N—SO₂—N—S—CCl₂F<br>　　　　　　　　　｜<br>　　　　　　　（p-tolyl） | | | 25 | 22 |

Mixture according to the invention:

| Mixing ratio | | Active compound application rate in g/ha | | Actual efficacy | Expected value, calculated using Colby's formula |
|---|---|---|---|---|---|
| (I)<br>+<br>Tolyfluanid | } | 1:10 | 2.5<br>+<br>25 } | 57 | 39 |

Sphaerotheca test (cucumber)/protective

| Active compound | Active compound application rate in g/ha | % efficacy |
|---|---|---|

| (I) | 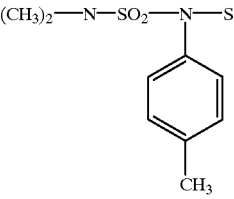 | 2.5 | 22 |
|---|---|---|---|
| Bitertanol (C) | 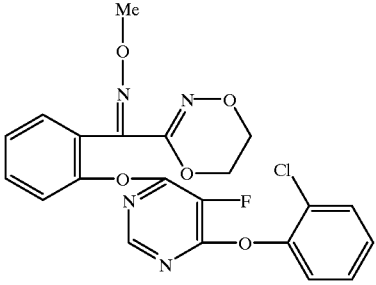 | 2.5 | 20 |

Mixture according to the invention:

| Mixing ratio | | Active compound application rate in g/ha | | Actual efficacy | Expected value, calculated using Colby's formula |
|---|---|---|---|---|---|
| (I)<br>+<br>Bitertanol | } | 1:1 | 2.5<br>+<br>2.5 } | 50 | 38 |

Sphaerotheca test (cucumber)/protective

| Active compound | Active compound application rate in g/ha | % efficacy |
|---|---|---|

TABLE 2-continued

| Active compound | | | | Active compound application rate in g/ha | | | % efficacy |
|---|---|---|---|---|---|---|---|

(I) — [structure: methoxyimino benzyl dihydrodioxazine / pyrimidine with 2-chlorophenoxy and F] — 2.5 — 22

Triadimefon (E) — [structure: (CH3)3C-C(=O)-CH(triazolyl)-O-(4-chlorophenyl)] — 2.5 — 30

Mixture according to the invention:

| Mixing ratio | | Active compound application rate in g/ha | | Actual efficacy | Expected value, calculated using Colby's formula |
|---|---|---|---|---|---|
| (I) + Triadimefon | 1:1 | 2.5 + 2.5 | | 67 | 45 |

Sphaerotheca test (cucumber)/protective

| Active compound | Active compound application rate in g/ha | % efficacy |
|---|---|---|

(I) — [structure as above] — 2.5 — 22

(δ) — [structure: tBu-cyclohexyl-spiro-dioxolane-CH2-N(Et)(Pro)] — 2.5 — 10

Mixture according to the invention:

| Mixing ratio | | Active compound application rate in g/ha | | Actual efficacy | Expected value, calculated using Colby's formula |
|---|---|---|---|---|---|
| (I) + (δ) | 1:1 | 2.5 + 2.5 | | 70 | 30 |

Sphaerotheca test (cucumber)/protective

| Active compound | Active compound application rate in g/ha | % efficacy |
|---|---|---|

TABLE 2-continued

| Active compound | Active compound application rate in g/ha | % efficacy |
|---|---|---|
| (I) [structure shown] | 2.5 | 22 |
| Captan (θ) [structure shown] | 12.5 | 0 |

Mixture according to the invention:

| Mixing ratio | | Active compound application rate in g/ha | | Actual efficacy | Expected value, calculated using Colby's formula |
|---|---|---|---|---|---|
| (I) + Captan | 1:5 | 2.5 + 12.5 | | 63 | 22 |

Sphaerotheca test (cucumber)/protective

| Active compound | Active compound application rate in g/ha | % efficacy |
|---|---|---|
| (I) [structure shown] | 2.5 | 22 |
| Pyrimethanil (Q) [structure shown] | 12.5 | 10 |

Mixture according to the invention:

| Mixing ratio | | Active compound application rate in g/ha | | Actual efficacy | Expected value, calculated using Colby's formula |
|---|---|---|---|---|---|
| (I) + Pyrimethanil | 1:5 | 2.5 + 12.5 | | 57 | 30 |

Sphaerotheca test (cucumber)/protective

| Active compound | Active compound application rate in g/ha | % efficacy |
|---|---|---|

TABLE 2-continued

| | | Mixture according to the invention: | | |
|---|---|---|---|---|
| | Mixing ratio | Active compound application rate in g/ha | Actual efficacy | Expected value, calculated using Colby's formula |

(I) 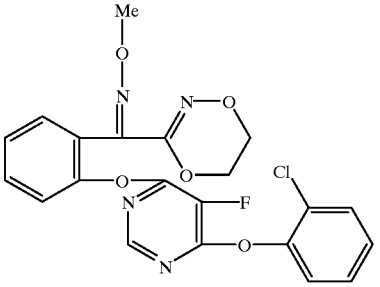 2.5 22

Azoxystrobin (U) 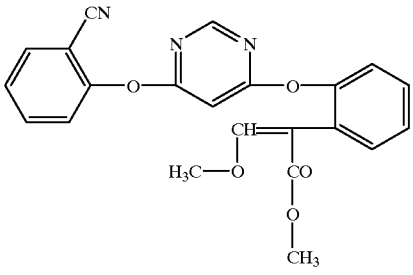 2.5 57

| Mixing ratio | Active compound application rate in g/ha | Actual efficacy | Expected value, calculated using Colby's formula |
|---|---|---|---|
| (I) + Azoxystrobin } 1:1 | 2.5 + 2.5 } | 83 | 66 |

EXAMPLE 3

Botrtis Test (Beans)/Protective

To test for protective activity, young plants are sprayed with the commercial active compound preparation at the stated application rate. After the spray coating has dried on, 2 small pieces of agar covered with *Botrytis cinerea* are placed on each leaf. The inoculated plants are placed in a darkened chamber at about 20° C. and 100% relative atmospheric humidity.

Two days after the inoculation, the size of the infected spots on the leaves is evaluated. 0% means an efficacy corresponding to that of the control, and an efficacy of 100% means that no infection is observed.

The good fungicidal activity of the active compound combinations according to the invention is evident from the example below. While the individual active compounds exhibit weaknesses with regard to the fungicidal activity, the combinations have an activity which exceeds a simple addition of activities.

A synergistic effect of fungicides is always present when the fungicidal activity of the active compound combinations exceeds the total of the activities of the active compounds when applied individually.

The expected activity for a given combination of two active compounds can be calculated as follows (cf. Colby, S. R., "Calculating Synergistic and Antagonistic Responses of Herbicide Combinations", Weeds 15, pages 20–22, 1967):

If

X is the efficacy expressed in % of the untreated control when applying active compound A in a concentration of m ppm, Y is the efficacy expressed in % of the untreated control when applying active compound B at a concentration of n ppm, E is the expected efficacy expressed in % of the untreated control when applying the active substances A and B at a concentration of m and n ppm, respectively, then $$E = X + Y - \frac{X \times Y}{100}$$

If the actual fungicidal activity exceeds the calculated value, then the activity of the combination is superadditive, i.e. a synergistic effect exists. In this case, the efficacy which was actually observed must be greater than the value for the expected efficacy (E) calculated from the abovementioned formula.

The table below clearly shows that the observed activity of the active compound combination according to the invention is greater than the calculated activity, i.e. a synergistic effect is present.

TABLE 3

Botrytis test (beans)/protective

| Active compound | Active compound application rate in g/ha | % efficacy |
|---|---|---|
| 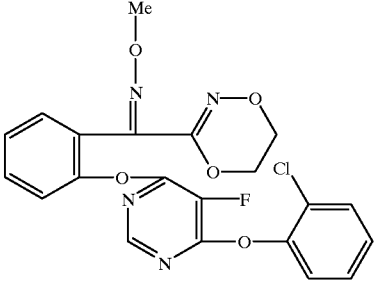 | 50 | 15 |
| fosethyl-Al (O)  $\left[ C_2H_5-O\diagdown_{H}P\diagup_{O}^{O} \right] \times 3 \times Al$ | 250 | 4 |

Mixture according to the invention:

| Mixing ratio | | Active compound application rate in g/ha | | Actual efficacy | Expected value, calculated using Colby's formula |
|---|---|---|---|---|---|
| (I) + fosethyl-Al | 1:5 | 50 + 250 | | 55 | 18 |

EXAMPLE 4

*Fusarlium nivale* Test (Triticale)/Seed Treatment

The active compounds are applied as a dry seed dressing. This is prepared by extending the respective active compound with ground mineral to give a finely pulveruient mixture which ensues uniform distribution on the seed surface.

To dress the seed, the infected seed together with the seed dressing is shaken for 3 minutes ini a sealed glass flask.

2×100 corns of triticale are sown at a depth of 1 cm in standard soil and cultivated in a greenhouse at a temperature of about 10° C. and a relative atmospheric humidity of about 95% in seed trays which receive a light regimen of 15 hours per day.

About 3 weeks after sowing, the plants are evaluated for symptoms of snow mould. 0% means an efficacy which corresponds to that of the untreated control, while an efficacy of 100% means that no disease is observed.

TABLE 4
Fusarium nivale test (triticale)/seed treatment
| Active compound | Active compound application rate in mg/kg of seed | Efficacy in % |
|---|---|---|
| 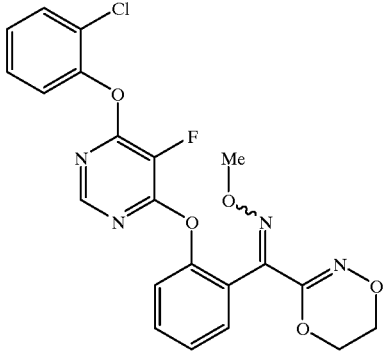 | 75 | 93 |
| (Tebuconazole) (O) | 25 | 89 |
| 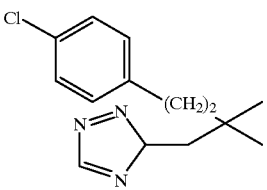 | 25 | 20 |
| (Triadimenol) (F) | 25 | 20 |
| 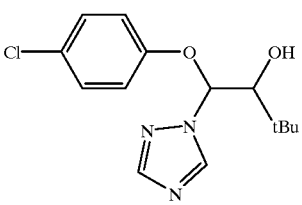 | 25 | 52 |
| (Pencycuron) P | 25 | 29 |
| 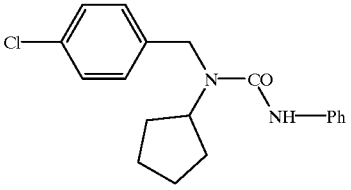 | 75 | 67 |
| (Fenpiclonil) V | | |
| 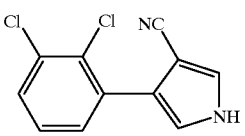 | | |

EXAMPLE 5

*Rihzoctonia solani* Test (Cotton)/Seed Treatment

The active compounds are applied as dry seed dressing. This is prepared by extending the respective active compound with ground mineral to give a finely pulverulent mixture which ensures uniform distribution on the seed surface.

To dress the seed, the infected seed together with the seed dressing is shaken for 3 minutes in a scaled glass flask.

2×50 corns of seed are sown at a depth of 2 cm into standard soil which is infected with *Rhizoctonia solani,* and the seeds are cultivated in a greenhouse at a temperature of about 22° C. in seed trays which receive a light regimen of 15 hours per day.

Evaluation is carried out after 8 days. 0% means an efficacy which corresponds to that of the untreated control, while an efficacy of 100% means that no disease is observed.

combination is mixed with the stated amounts of solvent and emulsifier, and the concentrate is diluted with water to the desired concentration.

To test for curative activity, young plants are dusted with spores of *Erysiphe graminis* f.sp. hordei. 48 hours after the inoculation, the plants are sprayed with the preparation of active compound at the stated application rate.

The plants are placed in a greenhouse at a temperature of about 20° C. and a relative atmospheric humidity of about 80%, in order to promote the development of mildew pustules.

Evaluation is carried out 7 days after the inoculation. 0% means an efficacy which corresponds to that of the control, whereas an efficacy of 100% means that no infection is observed.

TABLE 5

Rhizoctonia solani test (cotton)/seed treatment

| Active compound | Active compound application rate in mg/kg of seed | Efficacy in % |
|---|---|---|
| (I) 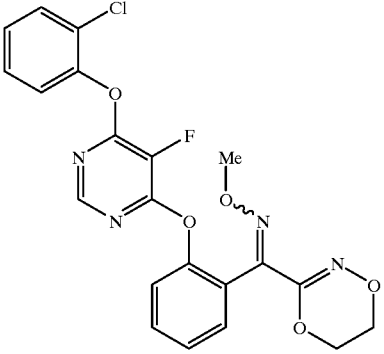 | 75 | 16 |
| (Triadimenol) (F) 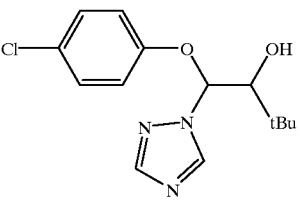 | 75 | 48 |
| Mixture according to the invention | | |
| (I) | 37.5 | |
| (F) | +37.5 | 63 |

EXAMPLE 6

Erysiphe Test (Barley)/Curative

Solvent: 25 parts by weight of N,N-dimethylacetamide
Emulsifier: 0.6 part by weight of alkylaryl polyglycol ether To produce a suitable preparation of active compound, 1 part by weight of active compound or active compound

TABLE 6

Erysiphe test (barley)/curative

| Active compound | Active compound application rate in g/ha | Efficacy in % |
|---|---|---|
| Known: | | |

| | | |
|---|---|---|
| (I) | 25 | 75 |
| | 12.5 | 33 |
| | 6.25 | 0 |
| (D) | 25 | 83 |
| | 6.25 | 33 |
| (F) | 6.25 | 67 |
| (V) | 12.5 | 92 |
| (W) | 6.25 | 33 |
| (T) | 12.5 | 67 |
| (δ) | 6.25 | 0 |
| Mixtures according to the invention | | |
| (I) + (D) | 6.25 + 18.75 | 100 |
| | 3.125 + 3.125 | 75 |
| | 18.75 + 6.25 | 92 |
| (I) + (F) | 1.563 + 4.687 | 83 |
| (I) + (T) | 6.25 + 6.25 | 75 |
| | 3.125 + 9.375 | 83 |
| | 9.375 + 3.125 | 83 |
| (I) + (V) | 6.25 + 6.25 | 100 |
| | 3.125 + 9.375 | 100 |
| (I) + (W) | 1.563 + 4.687 | 67 |
| (I) + (δ) | 3.125 + 3.125 | 50 |
| | 1.563 + 4.687 | 83 |

EXAMPLE 7

Erysiphe Test (Wheat)/Curative

Solvent: 25 parts by weight of N,N-dimethylacetamide
Emulsifier: 0.6 part by weight of alkylaryl polyglycol ether To produce a suitable preparation of active compound, 1 part by weight of active compound or active compound combination is mixed with the stated amounts of solvent and emulsifier, and the concentrate is diluted with water to the desired concentration.

To test for curative activity, young plants are dusted with spores of *Erysiphe graminis* f.sp. tritici. 48 hours after the inoculation, the plants are sprayed with the preparation of active compound at the stated application rate.

The plants are placed in a greenhouse at a temperature of about 20° C. and a relative atmospheric humidity of about 80%, in order to promote the development of mildew pustules.

Evaluation is carried out 7 days after the inoculation. 0% means an efficacy which corresponds to that of the control, whereas an efficacy of 100% means that no infection is observed.

TABLE 7

| Active compound | Active compound application rate in g/ha | Efficacy in % |
|---|---|---|
| Known: | | |
| (I) | 25 | 33 |
| | 6.25 | 0 |
| (T) | 6.25 | 0 |
| (R) | 25 | 17 |
| (Y) | 25 | 0 |
| Mixtures according to the invention | | |
| (I) + (T) | 3.125 + 3.125 | 50 |
| | 4.6875 + 1.5625 | 50 |
| (I) + (R) | 12.5 + 12.5 | 75 |
| | 18.75 + 6.25 | 50 |
| (I) + (Y) | 6.25 + 18.75 | 50 |
| | 18.75 + 6.25 | 50 |

EXAMPLE 8

*Leptosphaeria nodorum* Test (Wheat)/Curative

Solvent: 25 parts by weight of N,N-dimethylacetamide
Emulsifier: 0.6 part by weight of alkylaryl polyglycol ether To produce a suitable preparation of active compound, 1 part by weight of active compound or active compound combination is mixed with the stated amounts of solvent and emulsifier, and the concentrate is diluted with water to the desired concentration.

To test for curative activity, young plants are sprayed with a conidia suspension of *Leptosplhaeria nodorum*. The plants remain in an incubation cabin at 20° C. and 100% relative atmospheric humidity for 48 hours and are then sprayed with the preparation of active compound at the stated application rate.

The plants are placed in a greenhouse at a temperature of about 15° C. and a relative atmospheric humidity of about 80%.

Evaluation is carried out 10 days after the inoculation. 0% means an efficacy which corresponds to that of the control, whereas an efficacy of 100% means that no infection is observed.

TABLE 8

*Leptosphaeria nodorum* test (wheat)/curative

| Active compound | Active compound application rate in g/ha | Efficacy in % |
|---|---|---|
| Known: | | |
| (I) | 12.5 | 62 |
| | 6.25 | 62 |
| (F) | 6.25 | 25 |
| (W) | 12.5 | 25 |
| (T) | 12.5 | 50 |
| (δ) | 12.5 | 25 |
| (R) | 6.25 | 50 |
| Mixtures according to the invention | | |
| (I) + (F) | 4.6875 + 1.5625 | 75 |
| (I) + (W) | 9.375 + 3.125 | 75 |
| (I) + (T) | 9.375 + 3.125 | 75 |
| (I) + (δ) | 9.375 + 3.125 | 75 |
| (I) + (R) | 1.5625 + 4.6875 | 75 |

EXAMPLE 9

*Pyrenophora teres* Test (Barley)/Curative

Solvent: 25 parts by weight of N,N-dimethylacetamide
Emulsifier: 0.6 part by weight of alkylaryl polyglycol ether To produce a suitable preparation of active compound, 1 part by weight of active compound or active compound combination is mixed with the stated amounts of solvent and emulsifier, and the concentrate is diluted with water to the desired concentration.

To test for curative activity, young plants are sprayed with a conidia suspension of *Pyrenophora teres*. The plants remain in an incubation cabin at 20° C. and 100% relative atmospheric humidity for 48 hours. The plants are subsequently sprayed with the preparation of active compound at the stated application rate.

The plants are placed in a greenhouse at a temperature of about 20° C. and a relative atmospheric humidity of about 80%.

Evaluation is carried out 7 days after the inoculation. 0% means an efficacy which corresponds to that of the control, whereas an efficacy of 100% means that no infection is observed.

TABLE 9

| Active compound | Active compound application rate in g/ha | Efficacy in % |
|---|---|---|
| Known: | | |
| (I) | 6.25 | 0 |
| (F) | 6.25 | 0 |
| Mixtures according to the invention | | |
| (I) + (F) | 4.6875 + 1.5625 | 50 |

TABLE 10

Puccinia Test (Wheat)/Curative

Solvent: 25 parts by weight of N,N-dimethylacetamide

Emulsifier: 0.6 part by weight of alkylaryl polyglycol ether

To produce a suitable preparation of active compound, 1 part by weight of active compound or active compound combination is mixed with the stated amounts of solvent and emulsifier, and the concentrate is diluted with water to the desired concentration.

To test for curative activity, young plants are sprayed with a conidia suspension of *Puccinia recondita*. The plants remain in an incubation cabin at 20° C. and 100% relative atmospheric humidity for 48 hours. The plants are subsequently sprayed with the preparation of active compound at the stated application rate.

The plants are placed in a greenhouse at a temperature of about 20° C. and a relative atmospheric humidity of about 80%, in order to promote the development of rust pustules.

Evaluation is carried out 10 days after the inoculation. 0% means an efficacy which corresponds to that of the control, whereas an efficacy of 100% means that no infection is observed.

TABLE 10

Puccinia test (wheat)/curative

| Active compound | Active compound application rate in g/ha | Efficacy in % |
|---|---|---|
| Known: | | |
| (I) | 6.25 | 67 |
| (W) | 6.25 | 50 |
| (R) | 6.25 | 33 |
| Mixtures according to the invention | | |
| (I) + (W) | 1.5625 + 4.6875 | 83 |
| (I) + (R) | 3.125 + 3.125 | 75 |

EXAMPLE 11

Erysiphe Test (Wheat)/Protective

Solvent: 25 parts by weight of N,N-dimethylacetamide

Emulsifier: 0.6 part by weight of alkylaryl polyglycol ether

To produce a suitable preparation of active compound, 1 part by weight of active compound or active compound combination is mixed with the stated amounts of solvent and emulsifier, and the concentrate is diluted with water to the desired concentration.

To test for protective activity, young plants are sprayed with the preparation of active compound at the stated application rate.

After the spray coating has dried on, the plants are dusted with spores of *Erysiphe graminis* f.sp. tritici.

The plants are placed in a greenhouse at a temperature of about 20° C. and a relative atmospheric humidity of about 80%, in order to promote the development of mildew pustules.

Evaluation is carried out 7 days after the inoculation. 0% means an efficacy which corresponds to that of the control, whereas an efficacy of 100% means that no infection is observed.

TABLE 11

Erysiphe test (wheat)/curative

| Active compound | Active compound application rate in g/ha | Efficacy in % |
|---|---|---|
| Known: | | |
| (I) | 25 | 79 |
|  | 12.5 | 29 |
|  | 6.25 | 0 |
| (D) | 6.25 | 0 |
| (W) | 6.25 | 43 |
| (T) | 25 | 86 |
| (δ) | 6.25 | 14 |
| (R) | 12.5 | 0 |
| Mixtures according to the invention | | |
| (I) + (D) | 1.5625 + 4.6875 | 71 |
| (I) + (W) | 4.6875 + 1.5625 | 57 |
| (I) + (T) | 6.25 + 18.75 | 93 |
| (I) + (δ) | 3.125 + 3.125 | 57 |
|  | 1.5625 + 4.6875 | 79 |
|  | 4.6875 + 1.5625 | 57 |
| (I) + (R) | 3.125 + 9.375 | 57 |

EXAMPLE 12

*Leptosphaeria nodorum* Test (Wheat)/Protective

Solvent: 25 parts by weight of N,N-dimethylacetamide

Emulsifier: 0.6 part by weight of alkylaryl polyglycol ether

To produce a suitable preparation of active compound, 1 part by weight of active compound or active compound combination is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are sprayed with a spore suspension of *Leptosphaeria nodorum*. The plants remain in an incubation cabin at 20EC and 100% relative atmospheric humidity for 48 hours.

The plants are placed in a greenhouse at a temperature of about 1 5° C. and a relative atmospheric humidity of 80%.

Evaluation is carried out 10 days after the inoculation. 0% means an efficacy which corresponds to that of the control, whereas an efficacy of 100% means that no infection is observed.

TABLE 12

Leptosphaeria nodorum test (wheat)/protective

| Active compound | Active compound application rate in g/ha | Efficacy in % |
|---|---|---|
| Known: | | |
| (I) | 6.25 | 25 |
| (D) | 6.25 | 25 |
| (F) | 6.25 | 0 |
| (V) | 6.25 | 50 |
| (W) | 6.25 | 50 |
| (T) | 6.25 | 0 |
| (δ) | 6.25 | 25 |
| (R) | 6.25 | 25 |
| (Y) | 6.25 | 25 |
| Mixtures according to the invention | | |
| (I) + (D) | 3.125 + 3.125 | 50 |
| | 4.6875 + 1.5625 | 50 |
| (I) + (F) | 1.5625 + 4.6875 | 50 |
| | 1.5625 + 4.6875 | 100 |
| (I) + (W) | 3.125 + 3.125 | 100 |
| (I) + (T) | 4.6875 + 1.5625 | 50 |
| (I) + (δ) | 1.5625 + 4.6875 | 75 |
| | 4.6875 + 1.5625 | 100 |
| (I) + (R) | 3.125 + 3.125 | 100 |
| | 1.5625 + 4.6875 | 100 |
| | 4.6875 + 1.5625 | 100 |
| (I) + (Y) | 3.125 + 3.125 | 75 |
| | 1.5625 + 4.6875 | 100 |
| | 4.6875 + 1.5625 | 100 |

EXAMPLE 13

Puccinia Test (Wheat)/Protective

Solvent: 25 parts by weight of N,N-dimethylacetamide

Emulsifier: 0.6 part by weight of alkylaryl polyglycol ether

To produce a suitable preparation of active compound, 1 part by weight of active compound or active compound combination is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are sprayed with a conidia suspension of *Puccinia recondita*. The plants remain in an incubation cabin at 20° C. and 100% relative atmospheric humidity for 48 hours.

The plants are then placed in a greenhouse at a temperature of about 20° C. and a relative atmospheric humidity of 80%, in order to promote the development of rust pustules.

Evaluation is carried out 10 days after the inoculation. 0% means an efficacy which corresponds to that of the control, whereas an efficacy of 100% means that no infection is observed.

TABLE 13

Puccinia test (wheat)/protective

| Active compound | Active compound application rate in g/ha | Efficacy in % |
|---|---|---|
| Known: | | |

TABLE 13-continued

Puccinia test (wheat)/protective

| Active compound | Active compound application rate in g/ha | Efficacy in % |
|---|---|---|
| (I) | 6.25 | 81 |
| (D) | 6.25 | 38 |
| (F) | 6.25 | 13 |
| (V) | 6.25 | 81 |
| (W) | 6.25 | 75 |
| (T) | 6.25 | 25 |
| (δ) | 6.25 | 13 |
| (R) | 6.25 | 13 |
| (Y) | 6.25 | 13 |
| Mixtures according to the invention | | |
| (I) + (D) | 3.125 + 3.125 | 94 |
| | 1.5625 + 4.6875 | 94 |
| | 4.6875 + 1.5625 | 88 |
| (I) + (F) | 3.125 + 3.125 | 88 |
| (I) + (V) | 3.125 + 3.125 | 88 |
| | 1.5625 + 4.6875 | 100 |
| | 4.6875 + 1.5625 | 88 |
| (I) + (W) | 3.125 + 3.125 | 100 |
| | 1.5625 + 4.6875 | 88 |
| | 4.6875 + 1.5625 | 100 |
| (I) + (T) | 4.6875 + 1.5625 | 100 |
| (I) + (δ) | 3.125 + 3.125 | 100 |
| | 1.5625 + 4.6875 | 94 |
| | 4.6875 + 1.5625 | 100 |
| (I) + (R) | 3.125 + 3.125 | 94 |
| | 1.5625 + 4.6875 | 100 |
| | 4.6875 + 1.5625 | 100 |
| (I) + (Y) | 3.125 + 3.125 | 100 |
| | 1.5625 + 4.6875 | 94 |
| | 4.6875 + 1.5625 | 100 |

What is claimed is:

1. A fungicidal composition comprising a synergistically fungicidally effective amount of a combination of a first component and a second component, wherein said first component is a compound of the formula (I)

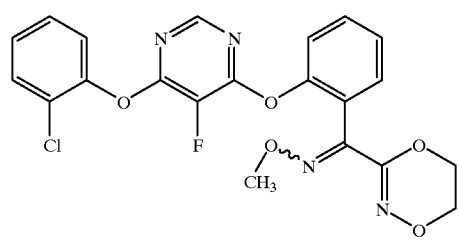

(I)

and wherein said second component is selected from the group consisting of:

Q pyrimethanil,

R cyprodinyl, and

S mepanipyrim.

2. The composition of claim 1, wherein the weight ratio of the first component to the second component 1:0.01 to 1:50.

3. The composition of claim 1, wherein said second components is pyrimethanil.

4. A process for preparing a fungicidal composition comprising the step of mixing a synergistic amount the a composition according to claim 1 with extenders and/or surfactants.

5. A method for combating fungi, comprising applying to the fungi or their environment a fungicidally effective amount of a synergistic fungicidal composition according to claim 1.

* * * * *